United States Patent
Khamnaen et al.

(10) Patent No.: US 9,556,286 B2
(45) Date of Patent: Jan. 31, 2017

(54) CATALYST FOR OLEFIN POLYMERIZATION, METHOD FOR ITS PREPARATION AND USE THEREOF

(71) Applicants: SCG CHEMICALS CO., LTD., Bangkok (TH); TERRAMARK MARKENCREATION GMBH, Bremen (DE)

(72) Inventors: Tossapol Khamnaen, Bangkok (TH); Sumate Charoenchaidet, Bangkok (TH)

(73) Assignee: SCG Chemicals Co., Ltd., Bangkok Metropolis (TH)

( * ) Notice: Subject to any disclaimer, the term of this patent is extended or adjusted under 35 U.S.C. 154(b) by 0 days.

(21) Appl. No.: 14/896,555

(22) PCT Filed: May 22, 2014

(86) PCT No.: PCT/EP2014/060569
§ 371 (c)(1),
(2) Date: Dec. 7, 2015

(87) PCT Pub. No.: WO2014/202329
PCT Pub. Date: Dec. 24, 2014

(65) Prior Publication Data
US 2016/0130371 A1    May 12, 2016

(30) Foreign Application Priority Data
Jun. 19, 2013 (EP) .................................. 13172833

(51) Int. Cl.
*C08F 4/76* (2006.01)
*C08F 4/64* (2006.01)
*C08F 4/6592* (2006.01)
*C07F 17/00* (2006.01)
*C08F 10/02* (2006.01)
*C07F 7/28* (2006.01)
*C08F 4/659* (2006.01)

(52) U.S. Cl.
CPC ............... *C08F 4/6592* (2013.01); *C07F 7/28* (2013.01); *C07F 17/00* (2013.01); *C08F 10/02* (2013.01); *C08F 4/65912* (2013.01); *C08F 4/76* (2013.01); *C08F 2420/04* (2013.01)

(58) Field of Classification Search
CPC ......... C08F 4/76; C08F 4/65912; C07F 17/00; C07F 17/28
See application file for complete search history.

(56) References Cited

U.S. PATENT DOCUMENTS

| | | | | |
|---|---|---|---|---|
| 3,387,010 A * | 6/1968 | Pande | ...................... | C07F 5/069 556/182 |
| 6,498,221 B1 * | 12/2002 | Nagy | ...................... | C08F 10/00 502/103 |
| 8,822,713 B2 * | 9/2014 | Longeau | ............... | C07C 251/48 526/240 |
| 2008/0306226 A1 * | 12/2008 | Boulanger | .......... | C07F 15/0066 526/90 |
| 2011/0152485 A1 * | 6/2011 | Boulanger | ........... | C07D 307/52 526/161 |
| 2012/0217432 A1 * | 8/2012 | Balland Longeau | . | C07C 251/48 252/62.54 |
| 2016/0122455 A1 * | 5/2016 | Berthoud | ................ | C07F 7/006 526/160 |

FOREIGN PATENT DOCUMENTS

EP    1426379 A1    6/2004

OTHER PUBLICATIONS

Sing, M.S., et al. "Some mononuclear titanium (IV) complexes of salicylidene anthranilic acid and o-vanillin oxime" Indian Journal of Chemistry, Section A: Inorganic, Bio-Inorganic, Physical, Theoretical & Analytical Chemistry, vol. 40A, No. 6, Jun. 28, 2001 (Jun. 28, 2001), pp. 633-637, XP009172971, in ISSN: 0376-4710 the whole document.

* cited by examiner

*Primary Examiner* — Rip A Lee
(74) *Attorney, Agent, or Firm* — Dorsey & Whitney LLP

(57) ABSTRACT

The invention relates to a catalyst for olefin polymerization represented by the general formula (1): wherein; M is a transition metal; $X^1$ and $X^2$ are independently selected from the group consisting of halide, alkyl group, aryl group, alkyl amine group, or alkyl aryl group, and are directly bond to M, $R^1$ and $R^2$ are independently selected from the group consisting of hydrogen, alkyl group or aryl group; and Cp is a cyclopentadienyl group.

$$R^1R^2C=N-OMC_pX^1X^2 \qquad (I)$$

20 Claims, No Drawings

CATALYST FOR OLEFIN POLYMERIZATION, METHOD FOR ITS PREPARATION AND USE THEREOF

FIELD OF THE INVENTION

The present invention relates to a catalyst for polymerization of olefins, as well as to method for its synthesis and its use in the polymerization of olefins.

BACKGROUND

For traditional Ziegler-Natta catalyst for olefin polymerization to produce an unimodal or bimodal product, the control of branching (comonomer) distribution by modifying this catalyst is quite difficult. Metallocene or single-site catalysts can dramatically change the distribution, and their technologies to produce fully functional unimodal/bimodal resin have recently been commercialized. For example, high performance bimodal polymers require a resin with very few branches in the lower molecular weight fractions and high concentration in higher molecular weight fractions. Such a control of comonomer distribution is important for resin grades such as pipe applications that require excellent environmental stress crack resistance (ESCR).

Since metallocene catalysts have been introduced, the number of advantages in the production of polyolefin copolymers using these catalysts offer a number of advantages including improved activity compared to traditional Ziegler Natta catalyst. Again metallocene catalysts are often described as being single-site in nature, the polyolefins produced with these catalysts are often very uniform in their molecular structure.

It is also well known that metallocene catalysts have been used for olefin polymerization to obtain a desired product.

Many metallocene catalysts have been disclosed. EP 0783022 B1 discloses the preparation of ethylene plastic using metallocene catalyst. EP 1598378 A1 also discloses a process for preparation of a multimodal polyethylene using metallocene catalyst.

EP 0971962 relates to a process for the polymerization of an olefin monomer and one or more comonomers to produce a polymer using a supported olefin polymerization catalyst system produced from catalyst component comprising a support material, a metallocene complex having transition metal of zirconium, and an activator.

EP067103 B2 relates to a ready-for-use supported olefin polymerization catalyst prepared by impregnation to obtain metallocene catalyst, $Cp_2ZrCl_2$, biscyclopentadienyl zirconium dichloride in MAO solution with an inorganic oxide as a catalyst support.

WO 00/40620 relates to bimodal polyethylene preparation using metallocene catalyst of either a bridged siloxy substituted bisindenyl zirconium dihalide compound or a catalyst comprising a monoalkyl substituted biscyclopentadienyl hafnium compound.

EP605952 discloses a process for producing polyethylene using metallocene catalyst such as bis(1,3-n-butyl cyclopentadienyl) zirconium dichloride and bis (1,3-dimethylcyclopentadienyl.

U.S. Pat. No. 6,242,545 relates to a process for the polymerization of monomer using hafnium transition metal metallocene catalyst. The hafnocene comprises at least cyclopentadienyl ligand including at least one linear or isoalkyl substituent of at least 3 carbon atom.

Even though the metallocene catalyst for olefin polymerization process is known and has been described, there is still a need for developing novel effective metallocene catalyst for olefin polymerization process.

Accordingly, it would be desired to provide an alternative metallocene catalyst within simple preparation and competitive cost. Further, an olefin polymerization catalyst shall be provided, having increased activity and allowing better control of branching of the polymer as well as of comonomer incorporation and distribution.

Further objective to be solved by the present invention are precise olefin polymerization, especially the evolution of new polymers with specified functions.

SUMMARY

Disclosed herein is a catalyst for olefin polymerization. The catalyst is represented by the general formula (I)

$$R^1R^2C=N-OMC_PX^1X^2,$$

wherein:
M is a transition metal;
$X^1$ and $X^2$ are independently selected from the group consisting of halide, alkyl group, aryl group, alkyl amine group, and alkyl aryl group, and wherein $X^1$ and $X^2$ are directly bonded to M;
$R^1$ and $R^2$ are independently selected from the group consisting of hydrogen, alkyl group, and aryl group; and
Cp is a cyclopentadienyl group.

DETAILED DESCRIPTION

The object has been solved by a catalyst for olefin polymerization represented by the general formula (I):

$$R^1R^2C=N-OMC_PX^1X^2$$

wherein;
M is a transition metal,
$X^1$ and $X^2$ are independently selected from the group consisting of halide, alkyl group, aryl group, alkyl amine group, or alkyl aryl group, and are directly bond to M,
$R^1$ or $R^2$ are independently selected from the group consisting of hydrogen, alkyl group or aryl group; and
Cp is a cyclopentadienyl group.

It is preferable if the metallocene used in the process according to the invention is titanocene and zirconocene or the mixture of these, preferably titanocene. In this regard, it is to be understood that the term "metallocene" is preferably a half sandwich complex, i.e. having only one cyclopentadienyl group attached to the metal.

Preferably, the transition metal is selected from Ti, Zr, or Hf.

Preferably, the alkyl group is C1 to C20 alkyl, more preferably C1 to C5 alkyl.

Preferably, the aryl is selected from unsubstituted or substituted aryl ring having 6-20 carbon atoms, more preferably 6-10 carbon atoms.

According to one preferred embodiment, the cyclopentadienyl group is selected from the group consisting of substituted or unsubstituted cyclopentadienyl group, substituted or unsubstituted cyclopentadienyl based fused aromatic compound, preferably indenyl or fluorenyl. The term cyclopentadienyl group includes cyclopentadienyl, indenyl and fluorenyl. The substituted cyclopentadienyl group can be mono- and polysubstituted type. The number of substituents is preferably at least 1 group, the number of substituents is preferably between 1 to 5 for cyclopentadienyl ligand, preferably 1 to 7 for indenyl ligand and preferably 1 to 9 for fluorenyl ligand.

According to another preferred embodiment, $R^1$ and $R^2$ form together an optionally substituted ring.

The object of the invention is also achieved by a method for the preparation of the inventive catalyst comprising the steps:
(a) reacting a ketone compound with a hydroxylamine to obtain oxime compound;
(b) reacting the oxime compound of step (a) with a base to obtain an activated oxime compound; and
(c) reacting the activated oxime compound of step (b) with a half sandwich metallocene compound to obtain the catalyst.

Preferably, the ketone compound in step (a) is selected from the group consisting of alkyl ketone, aryl ketone or mixed ketone (alkyl-aryl ketone).

Preferably, the base in step (b) is selected from organometallic or inorganic reagent, preferably alkyllithium and/or tert-butoxide.

According to an another preferred embodiment, step (b) is carried out in a solvent, preferably selected from hexane, toluene, diethylether or tetrahydrofuran (THF).

According to an another embodiment, metallocene compound is selected from cyclopentadienyl titanium trichloride, cyclopentadienyl zirconium trichloride, cyclopentadienyl hafnium trichloride, cyclopentadienyl titanium tribromide, cyclopentadienyl zirconium tribromide, cyclopentadienyl hafnium tribromide or pentamethyl cyclopentadienyl titanium trichloride.

Preferably, step (b) and/or step (c) are carried out at a temperature in the range from −80 to 50° C., more preferably temperature from −50 to 0° C. and even more preferably from −50 to −10° C.

The object of the invention is also achieved by a process for polymerization of olefins comprising the steps:
(a) reacting a mixture comprising at least one olefin, at least one inventive catalyst and at least one cocatalyst; and
(b) optionally adding at least one second olefin into the reaction mixture of step (a).

Preferably, the temperature in step (a) and/or (b) is 0 to 200° C., more preferably 5 to 100° C.

Preferably, the pressure in step (a) and/or (b) is 1 to 20 bar, more preferably 2-10 bar.

Preferably, the mixture of step (a) further comprises an aliphatic or aromatic hydrocarbons solvent.

The aliphatic hydrocarbon solvent could be saturated or unsaturated compound. Besides hydrogen, other elements could be bonded to carbon chain, for example oxygen, nitrogen, sulfur, and chloride. Moreover, the aliphatic hydrocarbon solvent could be linear, branched or cyclic structure. The aliphatic hydrocarbon solvent is selected form pentane, hexane, or hexene.

The olefin to be polymerized with the inventive method is preferably ethylene or ethylene with a further alpha-olefin, preferably a C3-C20 alpha olefin, more preferably C3-C9 alpha-olefin, such as propene, butene, hexene or octene. The catalyst can be used for homopolymerization or copolymerization.

According to a preferred embodiment, the cocatalyst is selected from organoaluminum compound and/or organoboron compound, preferably is methylaluminoxane.

The polymerization process according to the present invention may be used to prepare elastomeric co- and terpolymer of ethylene, propylene and optionally one or more diolefin monomer (diene). Typically, such elastomeric polymers will contain about 40 to about 80 wt % ethylene, 20 to 60 wt % propylene and up to 10 wt % of diolefin (diene monomer) respectively to obtain 100 wt % of polymer. The dienes may be selected from dicyclopentadiene (DCPD), 1,4-hexadiene (HD), 5-methylene-2-norbornene, 5-ethylidene-2-norbornene (ENB) and 5-vinyl-2-norbornene (VNB)

The polymer prepared according to the process of the present invention may have a weight average molecular weight of 10,000 to 5,000,000 g/mol. Preferably, the polymer may have weight average molecular weight of 20,000 to 1,000,000 g/mol, more preferably 50,000 to 300,000 g/mol.

It was surprisingly found that the catalyst of the present invention shows the advantage that the oxime ligands are commercially available or can be simply prepared by synthetic processes. A further advantage of the catalyst is its good solubility in hydrocarbon solvents. It was further surprisingly found that the inventive catalyst allows olefin polymerization to proceed with remarkable catalytic activity, stability and well controlled comonomer incorporation and distribution.

Further advantages and features of the invention will become apparent from the following detailed description of examples.

EXAMPLES

The following examples are illustrated as a method for oxime-containing metallocene catalyst preparation and using the same for polymerization. However, they are not to be considered in any way limitative of the invention. Numerous changes and modification can be made with respect to the invention.

Example 1

An oxime containing metallocene catalyst of the invention was prepared according to the following procedure.

Part I: Preparation of oxime compound (TPK001)

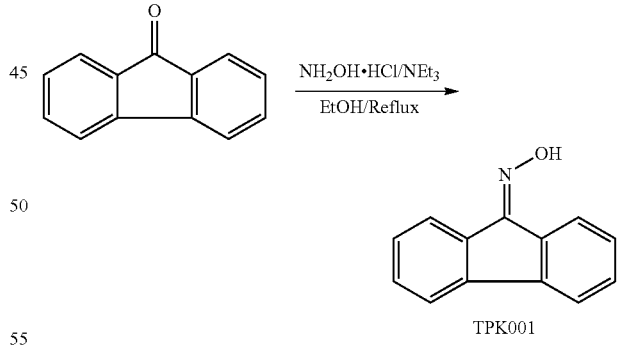

TPK001

In a 250-mL round-bottomed flask, triethylamine (NEt$_3$) (0.11 mol, 11.13 g) was added portion wise to a mixture of 9-fluorenone (0.1 mol, 18 g) and NH$_2$OH.HCl (0.11 mol, 7.65 g) in ethanaol (100 mL). The reaction mixture was then refluxed for 6 h. After cooling down, it was concentrated in vacuo. The solid residue was then taken up by EtOAc and extracted 3 times with H$_2$O. The combined organic layers were dried over anhydrous MgSO$_4$ and solvent was removed under vacuum. Recrystallization using EtOAc: Hexane obtained compound of fluorenone oxime, TPK001 (C$_{13}$H$_9$NO and MW 195.22) as a yellow needles. The NMR result: 1H NMR (300 MHz, CDCl₃) □=8.82 (bs, 1H, OH), 8.41 (d, 1H, ArH), 7.74 (d, 1H, ArH), 7.65 (dd, 2H, ArH), 7.40 (dd, 2H, ArH), 7.35 (d, 1H, ArH) and 7.30 (d, 1H, ArH).

Part II: Preparation of oxime metal compound (TPK002)

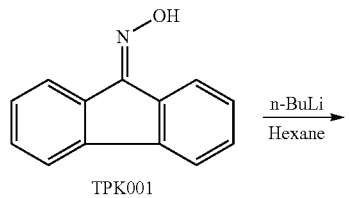

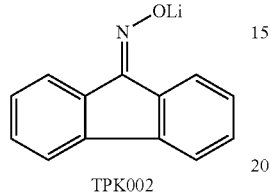

In a 100-mL round-bottomed flask, a suspension of TPK001 (3.9 g, 20 mmol) in hexane (50 mL) was cooled at −30° C. for 30 min n-BuLi (1.6 M in Hexane, 12.5 mL, 20 mmol) was added and the reaction mixture was further stirred at room temperature for 4 h. It was filtered and the solid was dried under vacuum to obtain oxime metal compound, TPK002 (Cl₃H₈LiNO, MW 201.15) as off-white solid.

Part III: Preparation of oxime containing metallocene catalyst (TPK003 and TPK004)

Synthesis of TPK003

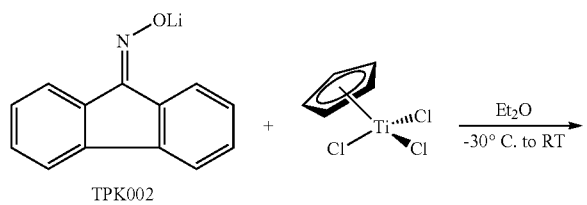

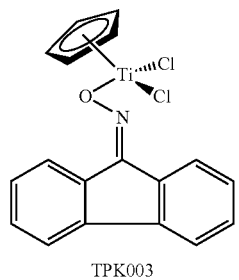

In a 50-mL round-bottomed flask, a solution of cyclopentadienyl titanium trichloride (438 mg, 2 mmol) in ethanol (25 mL) was cooled at −30° C. for 30 min TPK002 (406 mg, 2.02 mmol) was then added. The reaction mixture became a yellow suspension and was stirred for a further 6 h at room temperature. CH₂Cl₂ (3 mL) was then added while stirring in order to remove LiCl prior to filtration to obtain TPK003 (C₁₈H₁₃Cl₂NOTi, MW 378) as yellow solid. The NMR result: 1H NMR (300 MHz, CDCl3) □=8.26 (d, 1H, J 7.3 Hz, ArH), 7.96 (d, 1H, J 7.7 Hz, ArH), 7.67 (m, 2H, ArH), 7.51 (m, 2H, ArH), 7.39 (m, 2H, ArH) and 6.90 (s, 5H, CpH).

Synthesis of TPK004

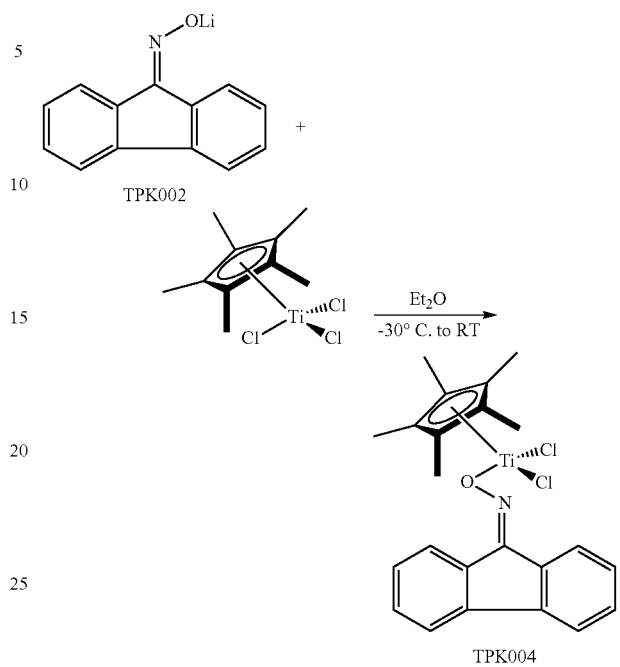

In a 50-mL round-bottomed flask, an orange solution of pentamethylcyclopentadienyl titanium trichloride (578 mg, 2 mmol) in ethanol (25 mL) was cooled at −30° C. for 30 min TPK002 (406 mg, 2.02 mmol) was then added. The reaction mixture became a red-orange suspension and was stirred for a further 6 h at room temperature. CH₂Cl₂ (3 mL) was then added during stirring in order to remove LiCl prior to filtration to obtain TPK004 (C₂₃H₂₃Cl₂NOTi) as red-orange solid. The NMR result: 1H NMR (300 MHz, CDCl3) □=8.34 (d, 1H, J 7.5 Hz, ArH), 7.96 (d, 1H, J 7.5 Hz, ArH), 7.57 (m, 2H, ArH), 7.44-7.20 (m, 4H, ArH) and 2.16 (s, 15H, CpCH3)

Example 2

Ethylene Polymerization Using "TPK004" Catalyst

Polymerization was done with 0.38 mg of the prepared catalyst (TPK004) with methylaluminoxane cocatalyst at the amount of 1 ml and ethylene pressure of 5 bars in 50 C toluene medium. After 30 minutes, the polymerization was discontinued by closing the feed of ethylene and by starting the cooling of the reactor. The yield of the reaction was 700 mg of polyethylene which gives the activities of 1400 kg PE/molTi·h. as the act of catalyst. When additionally, 1-hexene was fed to polymerization mixture process, it was found that the oxime-containing metallocene catalyst, TPK004, shows higher activity and comonomer content than Ziegler-Natta catalyst. As the Ziegler-Natta type catalyst MgCl₂—TiCl₄ was used. This catalyst can be prepared by (i) mixing MgCl₂ in ethanol and n-hexane to form reaction mixture (I), (ii) further reacting the reaction mixture (I) with organo aluminum (dietyl aluminum chloride) to form reaction mixture (II), (iii) adding TiCl₄ into reaction mixture (II) to form solid product (III), (iv) washing the solid product (III) with n-hexane and, (v) mixing the washed solid product (III) with n-hexane and carbontetrachloride to obtain catalyst component for olefin polymerization.

TABLE 1

| | Catalytic activity | | |
|---|---|---|---|
| Catalyst | Ethylene (bar) | Temperature (° C.) | Activity (kgPE/molTi · h) |
| Ziegler-Natta (comparative) | 8 | 85 | 650 |
| TPK004 | 5 | 50 | 1400 |

TABLE 2

| | Comonomer content | | | |
|---|---|---|---|---|
| Catalyst | Ethylene (bar) | Temperature (° C.) | 1-Hexene (ml) | 1-Hexene content (%) |
| Ziegler-Natta | 5 | 50 | 5 | n/a |
| TPK004 | 5 | 50 | 5 | 4.6 |

As demonstrated by example 2, the oxime-containing metallocene complex can be used as catalyst for olefin polymerization. In addition, design and synthesis the catalyst also gives good results in both activity and comonomer content as mentioned previously.

The feature disclosed in the foregoing description, and the claims, both separately and in any combination thereof, can be material for realizing the invention in diverse forms thereof.

The invention claimed is:

1. A catalyst for olefin polymerization represented by the general formula (I)

$R^1R^2C=N-OMC_pX^1X^2$, wherein:

M is a transition metal;

$X^1$ and $X^2$ are independently selected from the group consisting of halide, alkyl group, aryl group, alkyl amine group, and alkyl aryl group, and wherein $X^1$ and $X^2$ are directly bonded to M;

$R^1$ and $R^2$ are independently selected from the group consisting of hydrogen, alkyl group, and aryl group; and Cp is a cyclopentadienyl group.

2. The catalyst according to claim 1, wherein the metal is selected from the group consisting of Ti, Zr, and Hf.

3. The catalyst according to claim 1, wherein one or more of $X^1$, $X^2$, $R^1$, and $R^2$ is C1-C20 alkyl.

4. The catalyst according to claim 1, wherein one or more of $X^1$, $X^2$, $R^1$, and $R^2$ is an unsubstituted or substituted aryl ring having 6-20 carbon atoms.

5. The catalyst according to claim 4, wherein the aryl ring has 6-10 carbon atoms.

6. The catalyst according to claim 1, wherein the cyclopentadienyl group is selected from the group consisting of unsubstituted cyclopentadienyl and substituted cyclopentadienyl.

7. The catalyst according to claim 1, wherein $R^1$ and $R^2$ form together an optionally substituted ring.

8. The catalyst according to claim 1, wherein the cyclopentadienyl group is a cyclopentadienyl based fused aromatic compound.

9. The catalyst according to claim 8, wherein the cyclopentadienyl based fused aromatic compound is selected from the group consisting of indenyl and fluorenyl.

10. The catalyst according to claim 1, wherein the cyclopentadienyl group is substituted cyclopentadienyl having 6 to 20 carbon atoms.

11. A method for the preparation of a catalyst, the method comprising:
(a) reacting a ketone compound with hydroxylamine to obtain an oxime compound;
(b) reacting the oxime compound with a base to obtain an activated oxime compound; and
(c) reacting the activated oxime compound with a half sandwich metallocene compound to obtain the catalyst.

12. The method according to claim 11, wherein the ketone compound is selected from the group consisting of alkyl ketone and aryl ketone.

13. The method according to claim 11, wherein the base is selected from alkyllithium, potassium tert-butoxide, or mixtures thereof.

14. The method according to claim 11, wherein reacting the oxime compound with a base is carried out in a solvent selected from hexane, toluene, diethylether, tetrahydrofuran (THF) or a mixture thereof.

15. The method according to claim 11, wherein the metallocene compound is selected from cyclopentadienyl titanium trichloride, cyclopentadienyl zirconium trichloride, cyclopentadienyl hafnium trichloride, pentamethylcyclopentadienyl titanium trichloride, pentamethylcyclopentadienyl zirconium trichloride or pentamethylcyclopentadienyl hafnium trichloride.

16. The method according to claim 11, wherein reacting the oxime compound with a base is carried out at a temperature in the range from −80 to 50° C.

17. The method according to claim 11, wherein reacting the activated oxime compound with a half sandwich metallocene compound is carried out at a temperature in the range from −80 to 50° C.

18. A method for polymerization of olefins, the method comprising:
(a) forming a reaction mixture comprising at least one olefin, the catalyst of claim 1, and a cocatalyst; and
(b) optionally adding at least a second olefin to the reaction mixture.

19. The method according to claim 18, wherein the cocatalyst is selected from an organoaluminum or an organoboron compound.

20. The method according to claim 18, wherein the cocatalyst is methylaluminoxane.

* * * * *

UNITED STATES PATENT AND TRADEMARK OFFICE
CERTIFICATE OF CORRECTION

| | | |
|---|---|---|
| PATENT NO. | : 9,556,286 B2 | Page 1 of 1 |
| APPLICATION NO. | : 14/896555 | |
| DATED | : January 31, 2017 | |
| INVENTOR(S) | : Khamnaen et al. | |

It is certified that error appears in the above-identified patent and that said Letters Patent is hereby corrected as shown below:

In the Specification

Column 5, Line 64:
Delete "(300 MHz, CDC13)"
Insert --300 MHz, CDCl3--

Signed and Sealed this
Fourth Day of April, 2017

Michelle K. Lee
*Director of the United States Patent and Trademark Office*